United States Patent
Jee

(10) Patent No.: US 12,413,868 B2
(45) Date of Patent: Sep. 9, 2025

(54) PIXELATED MONOLITHIC PHOTOPLETHYSMOGRAPHIC SENSOR HAVING SPIKING NEURAL NETWORK STRUCTURE AND DRIVING METHOD THEREFOR

(71) Applicant: AJOU UNIVERSITY INDUSTRY-ACADEMIC COOPERATION FOUNDATION, Suwon-si (KR)

(72) Inventor: Dong Woo Jee, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 18/687,077

(22) PCT Filed: Oct. 13, 2022

(86) PCT No.: PCT/KR2022/015490
§ 371 (c)(1),
(2) Date: Feb. 27, 2024

(87) PCT Pub. No.: WO2023/101201
PCT Pub. Date: Jun. 8, 2023

(65) Prior Publication Data
US 2024/0380991 A1    Nov. 14, 2024

(30) Foreign Application Priority Data
Dec. 3, 2021 (KR) .................. 10-2021-0172377

(51) Int. Cl.
*H04N 25/10* (2023.01)
*H04N 25/77* (2023.01)

(52) U.S. Cl.
CPC ............ *H04N 25/10* (2023.01); *H04N 25/77* (2023.01)

(58) Field of Classification Search
CPC ............................ H04N 25/10; H04N 25/77
See application file for complete search history.

(56) References Cited

U.S. PATENT DOCUMENTS

| 10,579,925 B2 | 3/2020 | Kasabov et al. |
| 2016/0283842 A1 | 9/2016 | Pescianschi |
| 2020/0202206 A1 | 6/2020 | Rummens et al. |

FOREIGN PATENT DOCUMENTS

| KR | 10-1987399 B1 | 6/2019 |
| KR | 10-2020-0133246 A | 11/2020 |

OTHER PUBLICATIONS

Geon-Myeong Lee, "Behavior of Spiking Neuron Models and Learning of Spiking Neural Networks", Communications of the Korean Institute of Information Scientists and Engineers, Feb. 2020, pp. 8-19, vol. 38, No. 2.

(Continued)

*Primary Examiner* — On S Mung
(74) *Attorney, Agent, or Firm* — Sughrue Mion, PLLC

(57) ABSTRACT

A pixelated monolithic photoplethysmographic (PPG) sensor with a spiking neural network structure and a driving method thereof are disclosed. The pixelated monolithic photoplethysmographic (PPG) sensor according to an exemplary embodiment of the present disclosure includes a plurality of input neurons which generates spike signals and is disposed in at least one of a row direction and a column direction, a plurality of output neurons which adds the spike signals applied from the plurality of input neurons based on the column direction or the row direction and generates an output spike signal when the added result is equal to or higher than a predetermined reference value, and a synchro- (Continued)

nizer which converts each of the output spike signals into a digital signal.

10 Claims, 8 Drawing Sheets

(56) References Cited

OTHER PUBLICATIONS

Mostafa Rahimi Azghadi, et al., "Hardware Implementation of Deep Network Accelerators Towards Healthcare and Biomedical Applications", IEEE Transactions on Biomedical Circuits and Systems, Dec. 2020, pp. 1138-1159, vol. 14, No. 6.

International Search Report for PCT/KR2022/015490 dated Jan. 26, 2023 (PCT/ISA/210).

[Fig. 1]
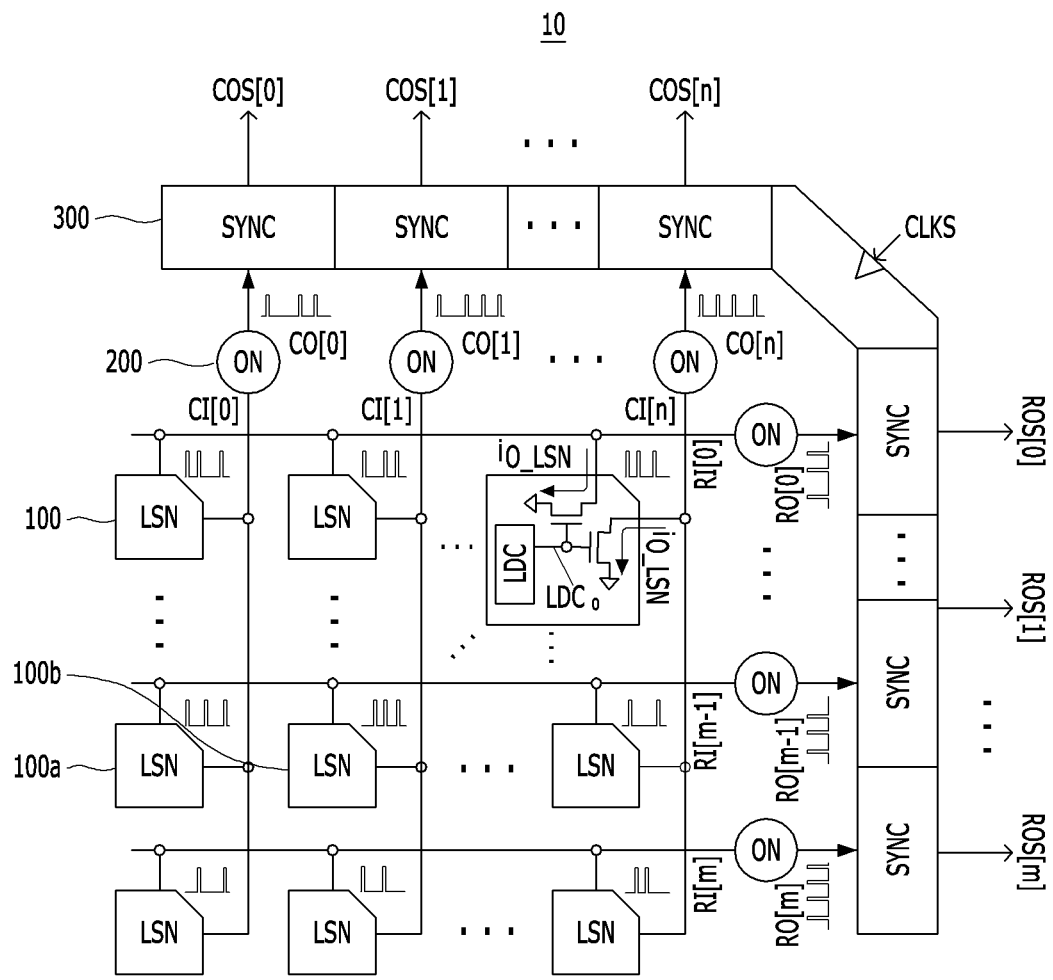

[Fig. 2]
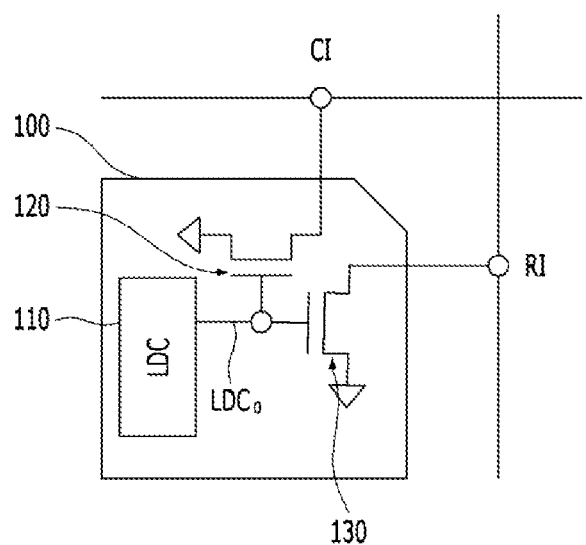

[Fig. 3]
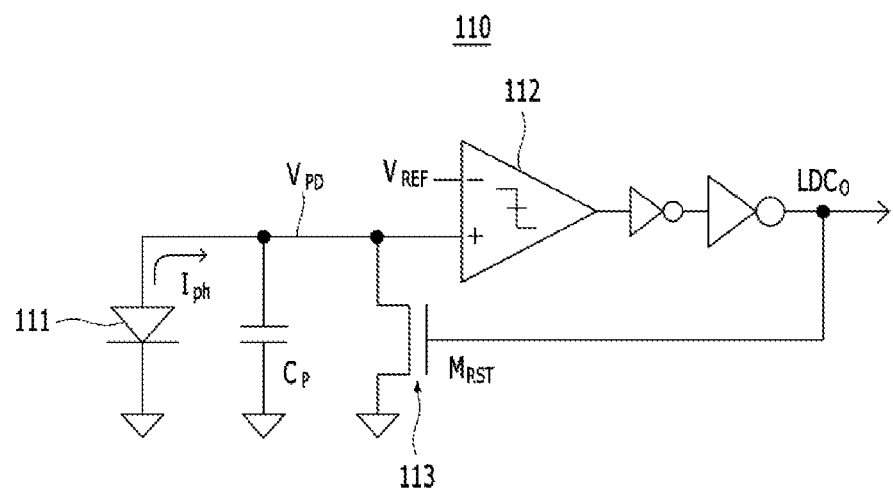

[Fig. 4]
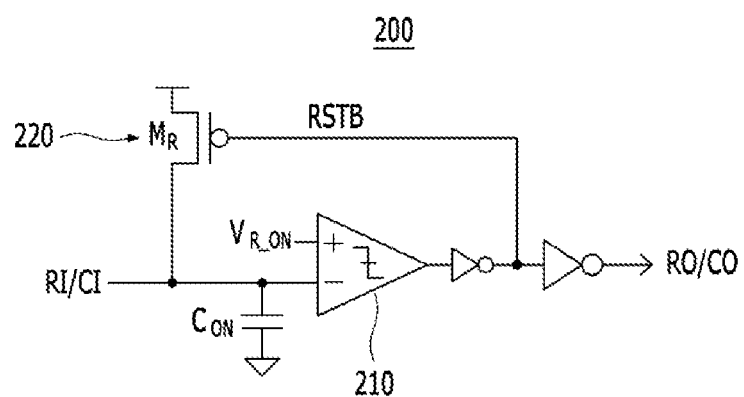

[Fig. 5]
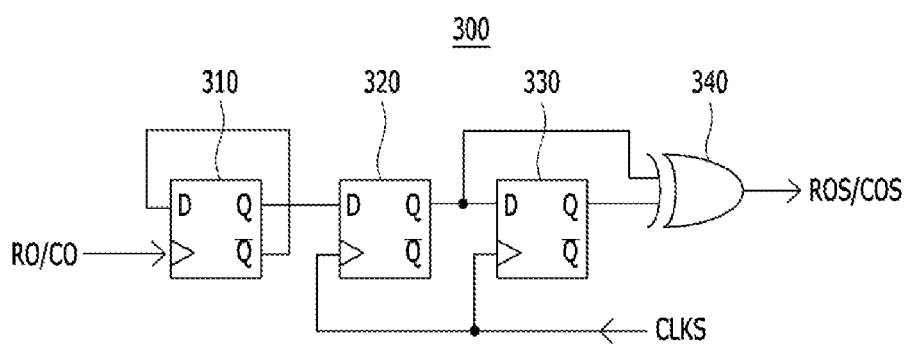

[Fig. 6]
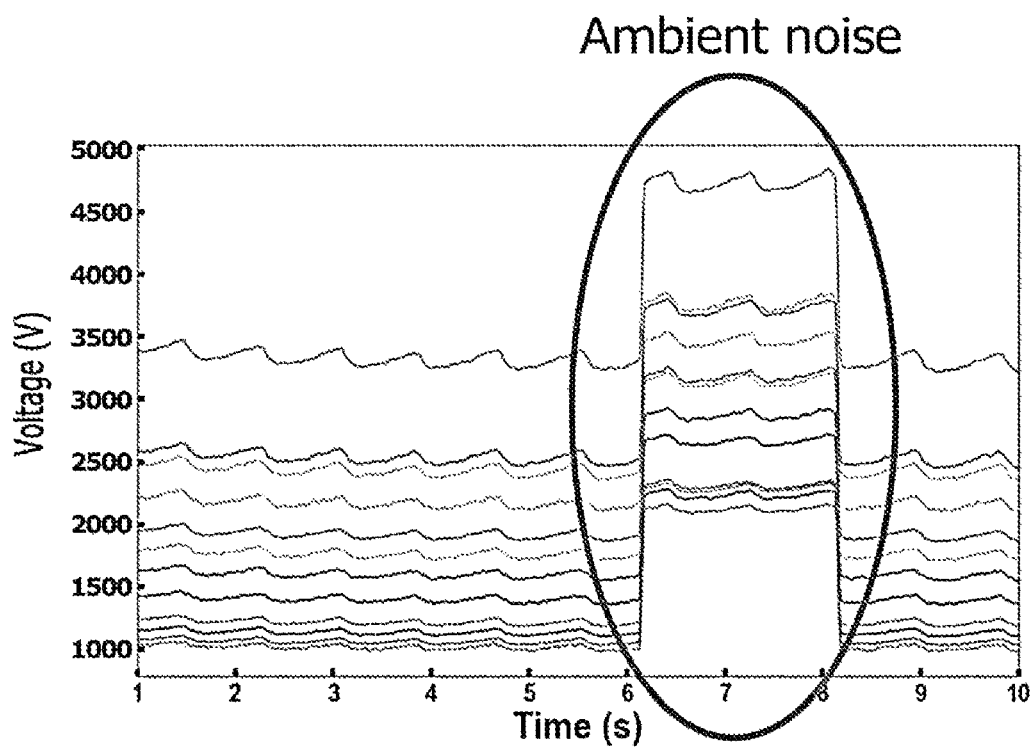

[Fig. 7]
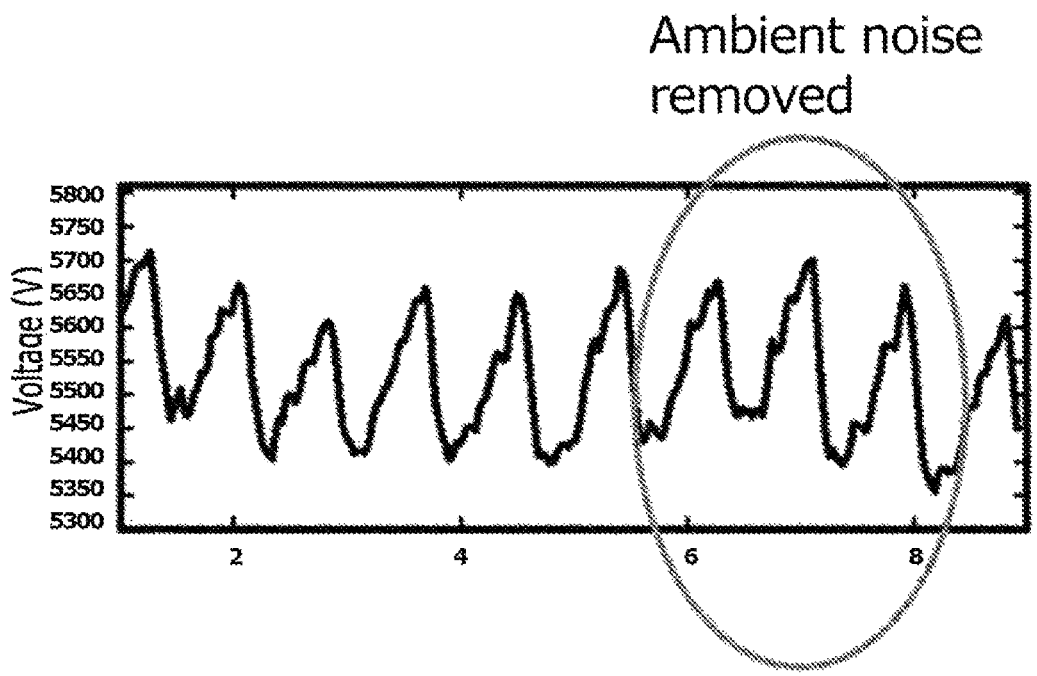

[Fig. 8]
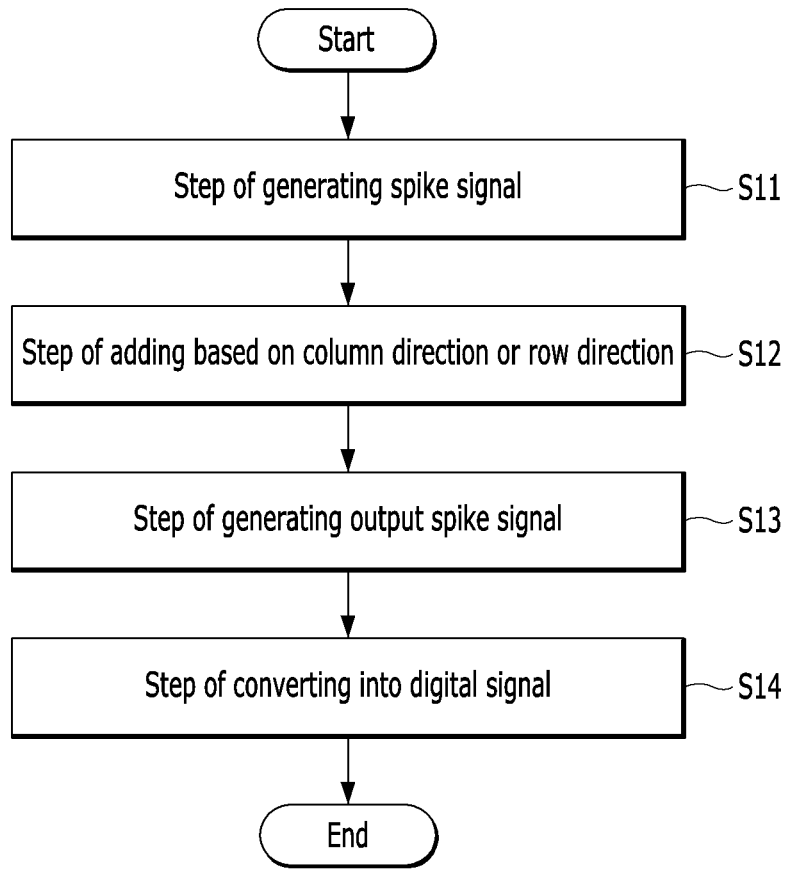

PIXELATED MONOLITHIC PHOTOPLETHYSMOGRAPHIC SENSOR HAVING SPIKING NEURAL NETWORK STRUCTURE AND DRIVING METHOD THEREFOR

CROSS REFERENCE TO RELATED APPLICATIONS

This application is a National Stage of International Application No. PCT/KR2022/015490 filed Oct. 13, 2022, claiming priority based on Korean Patent Application No. 10-2021-0172377 filed Dec. 3, 2021.

TECHNICAL FIELD

The present disclosure relates to a pixelated monolithic photoplethysmographic sensor having a spiking neural network structure and a driving method therefor.

BACKGROUND ART

Photoplethysmography (PPG) is a sensing technique which is the most frequently used for a wearable device to monitor a heart rate or measure an oxygen saturation. A main principle thereof is to measure changes in optical signals according to the change in blood flow so that the PPG sensor includes a photodiode (PD) which converts an optical signal into a current signal and a high performance analog front end (AFE) which converts the current signal into digital data. Recently, a monolithic CMOS PPG sensor in which both the PD and the AFE are implemented on a single die through a semiconductor-integrated circuit process has emerged to show excellent performance in various aspects, such as an available area, the number of components, and a signal-to-noise ratio.

The existing monolithic PPG sensor uses a distributed light-to-digital converter structure or uses a plurality of PDs which is disposed as an array to use a pin diode which is provided by a CMOS image sensor technique. The PPG signal is a change in a total sum of light applied to all PDs so that in order to maximize the signal-to-noise ratio of the PPG signal, a plurality of PD outputs is added by an analog circuit or a plurality of LDC outputs is added by a digital adder to generate a sensor output.

Each PD of the PD array receives a different light input depending on its position. For example, a PD which is close to a light source receives a strong light input and a PD which is far from the light source receives a weak light input. That is, if each PD output is independently processed, spatial information of the PPG signal may be obtained. When the spatial information is obtained, there is an advantage in that a signal processing technique, such as spatial filtering, is used to separate a noise caused by ambient light from the signal. However, it cannot be achieved by the PPG sensor of the related art.

When the AFE technique of the CMOS image sensor of the related art is used, an output of each PD may be individually extracted from the PD array. However, the CMOS image sensor time-divides the output of each PD pixel to transmit the output to the AFE so that this method is not appropriate for the PPG sensor which requires real-time output. Further, there is a disadvantage in that in order to implement the CMOS image sensor circuit, a lot of power is necessary.

A related art of the present disclosure is disclosed in Korean Registered Patent Publication No. 10-1987399.

DISCLOSURE

Technical Problem

In order to solve the above-described problem of the related art, an object of the present disclosure is to provide a pixelated monolithic photoplethysmographic (PPG) sensor with a spiking neural network structure which outputs a spike signal according to spatial information of each pixelated light sensing neuron (LSN) and a driving method of a sensor.

In order to solve the above-described problem of the related art, an object of the present disclosure is to provide a pixelated monolithic photoplethysmographic (PPG) sensor with a spiking neural network structure which combines a plurality of outputs acquired in response to a column direction or a row direction of the pixel structure to a single output without a separate adder and a driving method of a sensor.

In order to solve the above-described problem of the related art, an object of the present disclosure is to provide a pixelated monolithic photoplethysmographic (PPG) sensor with a spiking neural network structure which acquires an output from which a noise caused by ambient light is removed by a simple matrix operation without a complex signal processing technique of the related art and a driving method of a sensor.

However, technical objects to be achieved by various embodiments of the present disclosure are not limited to the technical objects as described above and other technical objects may be present.

Technical Solution

As a technical means to achieve the above-described technical object, a pixelated monolithic photoplethysmographic (PPG) sensor with a spiking neural network structure according to an exemplary embodiment of the present disclosure may include a plurality of input neurons which generates a spike signal and is disposed in at least one of a row direction and a column direction, respectively; a plurality of output neurons which adds the spike signals applied from the plurality of input neurons based on the column direction or the row direction and generates output spike signals when the added result is equal to or higher than a predetermined reference value; and a synchronizer which converts each of the output spike signal into a digital signal.

According to an exemplary embodiment of the present disclosure, each of the plurality of input neurons may include: a light-to-digital converter which generates the spike signal based on an intensity of received light; a first transistor which outputs the spike signal to a column input node corresponding to the column direction; and a second transistor which outputs the spike signal to a row input node corresponding to the row direction.

According to an exemplary embodiment of the present disclosure, the light-to-digital converter may generate the spike signal with a strength which is proportional to the intensity of the received light.

According to an exemplary embodiment of the present disclosure, the plurality of input neurons may be disposed to form an array including n×m pixels, the column input node may include n nodes to which the spike signal generated from m pixels corresponding to each column of the array is applied, and the row input node may include m nodes to which the spike signal generated from n pixels corresponding to each row of the array is applied.

According to an exemplary embodiment of the present disclosure, the plurality of output neurons may include n output neurons corresponding to any one of columns which form the array and m output neurons corresponding to any one of rows which form the array.

According to an exemplary embodiment of the present disclosure, the synchronizer may convert the output spike signal into a one-bit digital signal which is synchronized with a clock signal.

According to an exemplary embodiment of the present disclosure, relative spatial information for the PPG sensor of light which is applied to the plurality of input neurons may be derived based on magnitude information of the digital signal.

As a technical means to achieve the above-described technical object, a driving method of a pixelated monolithic photoplethysmographic (PPG) sensor with a spiking neural network structure according to an exemplary embodiment of the present disclosure may include generating a spike signal based on an intensity of light received by a plurality of input neurons; adding the spike signals applied from the plurality of input neurons based on a column direction or a row direction; generating output spike signals by a plurality of output neurons when an added result is equal to or higher than a predetermined reference value; and converting each of the output spike signals into a digital signal.

According to an exemplary embodiment of the present disclosure, in the generating of spike signals, a light-to-digital converter may generate the spike signal with a strength which is proportional to the intensity of received light and may output the spike signal to a column input node corresponding to the column direction and a row input node corresponding to the row direction.

According to an exemplary embodiment of the present disclosure, in the converting into a digital signal, the output spike signal may be converted into a one-bit digital signal which is synchronized with a clock signal.

The above-described solving means are merely illustrative but should not be construed as limiting the present disclosure. In addition to the above-described embodiments, additional embodiments may be further provided in the drawings and the detailed description of the present disclosure.

Advantageous Effects

According to the above-described solving means of the present disclosure, a pixelated monolithic photoplethysmographic (PPG) sensor with a spiking neural network structure which outputs a spike signal according to spatial information of each pixelated light sensing neuron (LSN) and a driving method thereof may be provided.

According to the above-described solving means of the present disclosure, the pixelated monolithic photoplethysmographic (PPG) sensor with a spiking neural network structure may combine a plurality of outputs acquired in response to a column direction or a row direction of the pixel structure to a single output without a separate adder.

According to the above-described solving means of the present disclosure, an output from which a noise caused by ambient light of the photoplethysmographic (PPG) sensor is removed may be obtained only by a simple matrix operation, without a complex signal processing technique of the related art.

However, the effect which can be achieved by the present disclosure is not limited to the above-described effects, there may be other effects.

DESCRIPTION OF DRAWINGS

FIG. 1 is a schematic diagram of a pixelated monolithic photoplethysmographic (PPG) sensor with a spiking neural network structure according to an exemplary embodiment of the present disclosure.

FIG. 2 is a view illustrating a schematic circuit diagram of an input neuron according to an exemplary embodiment of the present disclosure.

FIG. 3 is a view illustrating a circuit diagram of a light-to-digital converter according to an exemplary embodiment of the present disclosure.

FIG. 4 is a view illustrating a circuit diagram of an output neuron according to an exemplary embodiment of the present disclosure.

FIG. 5 is a view illustrating a circuit diagram of a synchronizer according to an exemplary embodiment of the present disclosure.

FIG. 6 is a graph illustrating photoplethysmographic (PPG) sensor data and a noise acquired using a pixelated monolithic photoplethysmographic (PPG) sensor according to an exemplary embodiment of the present disclosure.

FIG. 7 is a graph illustrating a result of removing a noise caused by ambient light using photoplethysmographic sensor data according to an exemplary embodiment of the present disclosure by utilizing spatial information.

FIG. 8 is a flowchart of an operation of a driving method of a pixelated monolithic photoplethysmographic (PPG) sensor with a spiking neural network structure according to an exemplary embodiment of the present disclosure.

BEST MODE

Hereinafter, the present disclosure will be described more fully with reference to the accompanying drawings so that those skilled in the art to which the present disclosure pertains can easily implement the exemplary embodiments of the present disclosure. However, the present disclosure can be realized in various different forms and is not limited to the embodiments described herein. Accordingly, in order to clearly explain the present disclosure in the drawings, portions not related to the description are omitted. Like reference numerals designate like elements throughout the specification.

Throughout the specification of the present disclosure, when it is described that an element is "coupled" to another element, the element may be "directly coupled" to the other element or "electrically coupled" or "indirectly coupled" to the other element through a third element.

Throughout the specification of the present disclosure, when one member is located "on", "above", "on an upper portion", "below", "under", and "on a lower portion" of the other member, the member may be adjacent to the other member, or a third member may be disposed between the above two members.

Throughout the specification of the present disclosure, unless explicitly described to the contrary, when it is described that an element "comprises" another element, it means that it may further include other elements rather than excluding other elements.

The present disclosure relates to a pixelated monolithic photoplethysmographic sensor with a spiking neural network structure and a driving method thereof.

Hereinafter, for the convenience of description, a pixelated monolithic photoplethysmographic (PPG) sensor 10 according to an exemplary embodiment of the present disclosure is referred to as a PPG sensor 10.

FIG. 1 is a schematic diagram of a pixelated monolithic photoplethysmographic (PPG) sensor with a spiking neural network structure according to an exemplary embodiment of the present disclosure.

Referring to FIG. 1, the PPG sensor 10 may include a plurality of input neurons 100, a plurality of output neurons 200, and a plurality of synchronizers 300.

Referring to FIG. 1, the PPG sensor 10 may include a plurality of input neurons 100, each of which is configured by a light sensing neuron (LSN). In other words, in the description of the exemplary embodiment of the present disclosure, the reference numeral 100 may be used interchangeably for a light sensing neuron (LSN) 100 and an input neuron 100.

Referring to FIG. 1, the input neuron 100 may be disposed in at least one of a column direction and a row direction. In other words, the plurality of input neurons 100 may be disposed to form an array including n×m pixels but is not limited thereto.

The column direction according to the exemplary embodiment of the present disclosure may be a horizontal direction (3 o'clock direction to 9 o'clock direction) with respect to a matter illustrated in FIG. 1, and in contrast, the row direction may be a vertical direction (12 o'clock direction to 6 o'clock direction).

However, such direction setting may vary depending on the placement state of the device of the present disclosure. For example, if necessary, based on FIG. 1, the PPG sensor 10 disclosed in the present disclosure may be disposed such that the row direction is directed to a horizontal direction or an oblique inclination direction and the column direction is directed to a vertical direction or an oblique inclination direction.

According to the exemplary embodiment of the present disclosure, each input neuron 100 may receive light and generate a spike signal which is proportional to an intensity of the received light. The input neural 100 will be described in more detail below with reference to FIGS. 2 and 3.

Further, according to the exemplary embodiment of the present disclosure, the generated spike signal may be output to a column input node CI in the column direction or a row input node RI of the row direction. In other words, each of the plurality of input neurons 100 may be disposed to be connected to one column input node CI and one row input node RI.

According to an exemplary embodiment of the present disclosure, the column input node CI may include n nodes to which spike signals generated from m pixels corresponding to each column of the above-described array are applied and the row input node RI may include m nodes to which spike signals generated from n pixels corresponding to each row of the above-described array are applied.

Specifically, the column input node CI may include CI[0], CI[1], . . . , CI[n] of FIG. 1 and the row input node RI may include RI[0], RI[1], . . . , RI[n], but is not limited thereto.

Further, referring to FIG. 1, the PPG sensor 10 may include a plurality of output neurons 200, each of which is configured by an output neuron (ON). In other words, in the description of the exemplary embodiment of the present disclosure, the reference numeral 200 may be used interchangeably for ON 200 and an output neuron 200.

Referring to FIG. 1, the plurality of output neurons 200 may include n output neurons 200 each corresponding to any one of columns which form an array and m output neurons 200 each corresponding to any one of rows which form an array. For example, when n and m are 12, there are a total of 24 output neurons 200 including 12 output neurons disposed in a column direction and 12 output neurons disposed in a row direction but are not limited thereto.

Further, referring to FIG. 1, CO[0], CO[1], . . . , CO[n] may refer to output terminals of the output neuron 200 which receives a spike signal from the column input node CI and RO[0], RO[1], . . . , RO[n] may refer to output terminals of the output neuron 200 which receives a spike signal from the row input node RI.

According to the exemplary embodiment of the present disclosure, each output neuron 200 may add spike signals applied from the plurality of input neurons 100 based on a column direction or a row direction. That is, the output neuron 200 may add the spike signals input from the plurality of column input nodes CI or add the spike signals input from the plurality of row input nodes RI. In the above-described example, any one output neuron 200 which performs the addition based on the column direction may add spike signals applied from 12 input neurons 100 but is not limited thereto.

Further, according to the exemplary embodiment of the present disclosure, when a result of adding spike signals applied from the input neuron 100 along the row direction or the column direction is equal to or higher than a predetermined reference value, the output neuron 200 may generate an output spike signal. That is, the output neuron 200 may output an output spike signal having a strength proportional to an intensity of light received by the input neuron 100. The output neuron 200 will be described in more detail below with reference to FIG. 4.

According to the exemplary embodiment of the present disclosure, the input neuron 100 and the output neuron 200 operate without being synchronized with a clock so that the PPG sensor 10 disclosed in the present disclosure may include a synchronizer 300 to synchronize and process the output spike signal with a digital signal.

Referring to FIG. 1, an input terminal of each synchronizer (SYNC) 300 may be provided to be connected to an output terminal of the output neuron 200. Referring to FIG. 1, one output neuron 200 and one synchronizer 300 are connected so that the number of synchronizers 300 and the number of output neurons 200 may be equal but are not limited thereto.

Further, referring to FIG. 1, COS[0], COS[1], . . . , COS[n] may refer to output terminals of the synchronizers 300 which receive the output spike signals from CO[0], CO[1], . . . , CO[n] and ROS[0], ROS[1], . . . , ROS[n] may refer to output terminals of the synchronizers 300 which receive the output spike signals from RO[0], RO[1], . . . , RO[n].

According to the exemplary embodiment of the present disclosure, the synchronizer 300 may receive the output spike signals from the output neuron 200 and convert each of the received output spike signals into a digital signal. Specifically, the synchronizer 300 may receive a clock signal and convert the output spike signal into one-bit digital signal synchronized with the received clock signal. The synchronizer 300 will be described in more detail below with reference to FIG. 5.

According to the exemplary embodiment of the present disclosure, the synchronizer 300 may convert each of the output spike signals which is proportional to an intensity of light received by the plurality of input neurons 100 into a digital signal.

For example, referring to FIG. 1, when an arbitrary input neuron 100, among the plurality of input neurons 100, that is, a plurality of light sensing neurons (LSN) 100 is specified as a first LSN 100a and the other one input neuron 100 is specified as a second LSN 100b, the first LSN 100a and the second LSN 100b may receive light with different intensities and generate spike signals with different strengths proportional to the intensity of the received light. Further, a column input node connected to the first LSN 100a is CI[0] and a column input node connected to the second LSN 100b is CI[1] so that the column input nodes are different. Therefore, the output spike signal generated in the output neuron 200 which receives each spike signal and a digital signal which is converted by the synchronizer 300 which receives each output spike signal may also have different magnitudes (strength).

Accordingly, the PPG sensor 10 according to the exemplary embodiment of the present disclosure may output a spike signal (or an output spike signal) according to spatial information of each pixelated light sensing neuron (LSN) 100 and a digital signal obtained by converting the spike signal. To be specific, the PPG sensor 10 generates a plurality of output data in which information about a pattern of light applied with different intensities to each of the plurality of input neurons 100 (for example, a characteristic, etc. in which an intensity of light incident onto an input neuron 100 which is relatively close to a light source is larger than an intensity of light incident onto another input neuron 100 which is relatively far from the light source) is spatially added in the column direction or the row direction to be utilized to identify specific spatial information of incident light which is applied to each of input neurons LSN in the pixel unit which forms the PPG sensor 10 through the analysis of each output.

In other words, an intensity of light applied to each of the plurality of light sensing neurons LSN 100 may be individually identified based on each spike signal (or an output spike signal) which is output and the digital signal using the PPG sensor 10 disclosed in the present disclosure. In other words, the PPG sensor 10 may derive relative spatial information of light applied to the plurality of input neurons 100 with respect to the PPG sensor, based on magnitude information of each digital signal which is converted in the synchronizer 300.

Further, according to the exemplary embodiment of the present disclosure, the PPG sensor 10 adds and outputs a plurality of outputs according to the spatial information of light in the form of a matrix or a vector to easily remove a noise caused by the ambient light.

FIG. 2 is a view illustrating a schematic circuit diagram of an input neuron according to an exemplary embodiment of the present disclosure.

Referring to FIG. 2, the input neuron 100 according to the exemplary embodiment of the present disclosure may include a light-to-digital converter (LDC) 110, a first transistor 120, and a second transistor 130.

According to the exemplary embodiment of the present disclosure, the light-to-digital converter 110 may receive light and generate a spike signal based on an intensity of the received light. Specifically, the light-to-digital converter 110 may generate a spike signal proportional to an intensity of light.

According to the exemplary embodiment of the present disclosure, the first transistor 120 may output a spike signal (LDCo, LDC output) generated in the light-to-digital converter 110 to a column input node CI corresponding to the column direction and the second transistor 130 may output a spike signal generated in the light-to-digital converter 110 to a row input node RI corresponding to the row direction.

Even though in FIG. 2, the first transistor 120 and the second transistor 130 are illustrated as N channel MOSFETs but are not limited thereto.

FIG. 3 is a view illustrating a circuit diagram of a light-to-digital converter according to an exemplary embodiment of the present disclosure.

Referring to FIG. 3, the light-to-digital converter 110 may include a photo diode 111, a first comparator 112, a first reset MOSFET $M_{RST}$ 113, and the like.

According to the exemplary embodiment of the present disclosure, the photo diode 111 may convert light energy into electric energy and $V_{PD}$ may refer to an output voltage by the photo diode 111. Further, according to the exemplary embodiment of the present disclosure, a cathode terminal of the photo diode 111 may be grounded and an anode terminal may not be biased, but they are not limited thereto.

According to the exemplary embodiment of the present disclosure, the first comparator 112 compares a reference voltage $V_{REF}$ and an output voltage $V_{PD}$ of the photo diode 111. When the output voltage $V_{PD}$ is equal to or higher than the reference voltage $V_{REF}$, the comparator may output a spike signal LDCo which is a positive value and when the output voltage $V_{PD}$ is lower than the reference voltage $V_{REF}$, the comparator may output a spike signal LDCo which is a negative value or zero but is not limited thereto.

According to the exemplary embodiment of the present disclosure, the first reset MOSFET 113 may reset a value applied to a non-inverting terminal (+ terminal) of the first comparator 112 based on the spike signal LDCo applied to the gate GATE. In FIG. 3, the first reset MOSFET 113 is illustrated as an N channel MOSFET but is not limited thereto.

Specifically, when the first reset MOSFET 113 is an N channel MOSFET, if the spike signal LDCo is a positive value, a positive value is applied to the gate GATE of the first reset MOSFET 113 and the first reset MOSFET 113 is turned on to conduct the non-inverting terminal (+ terminal) of the first comparator 112 and a ground terminal but is not limited thereto.

FIG. 4 is a view illustrating a circuit diagram of an output neuron according to an exemplary embodiment of the present disclosure.

Referring to FIG. 4, the output neuron (ON) 200 may receive a result of adding spike signals output from the plurality of column input nodes CI or the plurality of row input nodes RI. In other words, the output neuron 200 may add the spike signals based on the column direction or the row direction.

Hereinafter, for the convenience of description, referring to FIG. 4, a result of adding spike signals which are input to the output neuron 200 is specified as an input signal RI/CI.

Further, referring to FIG. 4, the output neuron 200 may include a second comparator 210, a second reset MOSFET $M_R$ 220, and the like.

According to the exemplary embodiment of the present disclosure, the second comparator 210 receives a predetermined reference value $V_{R\_ON}$ and the input signal RI/CI and compares the input reference value $V_{R\_ON}$ and the input signal RI/CI to generate an output spike signal RO/CO.

For example, when the input signal RI/CI is equal to or higher than the reference value $V_{R\_ON}$, the output spike signal RO/CO may be output as a positive value and in contrast, when the input signal RI/CI is lower than the reference value $V_{R\_ON}$, the output spike signal RO/CO may be output as a negative value or 0, but it is not limited thereto.

According to the exemplary embodiment of the present disclosure, the output value of the second comparator 210 may be inverted through a NOT gate and the inverted signal may be applied to the gate GATE of the second reset MOSFET 220. That is, the signal applied to the gate GATE of the second reset MOSFET 220 may be an inverted value RO'/CO' of the output spike signal.

According to the exemplary embodiment of the present disclosure, the second reset MOSFET 220 may reset a value applied to a non-inverting terminal (+ terminal) of the second comparator 210 based on the inverted output spike signal RO'/CO' applied to the gate GATE. In FIG. 4, the second reset MOSFET 220 is illustrated as a P channel MOSFET but is not limited thereto.

Specifically, when the second reset MOSFET 220 is a P channel MOSFET, if the inverted output spike signal RO'/CO' is a negative value, a negative value is applied to the gate GATE of the second reset MOSFET 220 and the first reset MOSFET 113 is turned on to conduct the non-inverting terminal (+ terminal) of the second comparator 210 and a ground terminal, but is not limited thereto.

FIG. 5 is a view illustrating a circuit diagram of a synchronizer according to an exemplary embodiment of the present disclosure.

Referring to FIG. 5, the synchronizer 300 may include a first flip flop 310, a second flip flop 320, a third flip flop 330, and an XOR gate 340.

For example, the first flip flop 310, the second flip flop 320, and the third flip flop 330 may be D-flip flops which are triggered by a rising edge of an input clock to operate but are not limited thereto.

Referring to FIG. 5, in the first flip flop 310, the output spike signal RO/CO is input to the clock terminal and the input terminal, and the inverted output terminal may be connected. Accordingly, in the first flip flop 310, the input terminal and the inverted output terminal are connected to each other so that the output is inverted as the output spike signal RO/CO is generated.

Further, in the second flip flop 320, the clock signal CLKS is input to the clock terminal and the input terminal may be connected to the output terminal of the first flip flop 310. The output of the second flip flop 320 is determined by the clock signal CLKS so that the second flip flop may serve to synchronize the output spike signal RO/CO which is generated at a random timing with the clock signal CLKS which is a reference clock signal.

Further, in the third flip flop 330, the clock signal CLKS is input to the clock terminal and the input terminal may be connected to the output terminal of the second flip flop 320. The third flip flop 330 delays the output of the second flip flop 320 by one clock to generate a subsequent signal for detecting an XOR gate 340.

Further, the XOR gate 340 receives inputs from an output terminal of the second flip flop 320 and an output terminal of the third flip flop 330 to output a one-bit digital signal. The output signal of the second flip flop 320 and the output signal of the third flip flop 330 are one clock different from the clock signal CLKS so that a digital signal with a constant magnitude may be generated.

FIG. 6 is a graph illustrating photoplethysmographic (PPG) sensor data and noise acquired using a pixelated monolithic photoplethysmographic (PPG) sensor according to an exemplary embodiment of the present disclosure.

Referring to FIG. 6, it is confirmed that the PPG sensor data includes different output voltages for every intensity of the received light. Here, it means that the higher the voltage (for example, a high DC value or AC value) is output, the closer the pixel or the input neuron 100 is to the light source. That is, it shows that the PPG sensor 10 according to the exemplary embodiment of the present disclosure may output a spike signal according to spatial information of each pixelated light sensing neuron (LSN) 100.

Further, referring to FIG. 6, it is confirmed that a noise is caused in the period of 6 to 8 seconds due to ambient light (ambient noise).

FIG. 7 is a graph illustrating a result of removing a noise caused by ambient light using photoplethysmographic sensor data according to an exemplary embodiment of the present disclosure by utilizing spatial information.

Referring to FIG. 7, the PPG sensor 10 may convert each output voltage which is individually output into an output from which the noise caused by the ambient light is removed by a simple matrix operation without a complex signal processing technique of the related art. Specifically, referring to an "ambient noise removed" period illustrated in FIG. 7, it is confirmed that single output data (data obtained by combining a plurality of output data derived respectively along a row direction and/or a column direction as one sequence) from which influence due to a noise present in the period of 6 to 8 seconds of the graph of FIG. 6 is removed may be derived.

That is, according to the exemplary embodiment of the present disclosure, the PPG sensor 10 may acquire an output from which the noise caused by the ambient light is removed based on spatial information of light and a plurality of outputs.

To be more specific, according to the exemplary embodiment of the present disclosure, when the change in each output (for example, a voltage value, etc. corresponding to a digital signal output for each row or column of a pixel array) generated by the PPG sensor 10 is time-sequentially analyzed, a period in which an output value is rapidly changed as compared with preceding and following sequences due to the noise caused by the interference, etc. of the ambient light may be sensed (detected) and the PPG sensor 10 applies a predetermined correcting process to output data including the noise to derive a normal output from which a noise for the corresponding period is removed.

For example, the PPG sensor 10 may mount (include) a correction module (not illustrated) which operates to derive a normal output from which a noise is removed by defining a plurality of outputs generated so as to correspond to the incident light as an output matrix corresponding to a pixel array and performing a matrix multiplication on a reference matrix to remove the noise for the output matrix.

To be more specific, when 12 outputs which are displayed with different shapes (colors, etc.) are a plurality of output data generated so as to correspond to each of 12 columns or rows in FIG. 6, the entire output of the PPG sensor 10 may be combined in the form of 12×1 matrix. The correction module (not illustrated) of the PPG sensor 10 performs the matrix multiplication on the reference matrix with a magnitude of 1×12 in which each element is determined with a value which removes a noise for the above-described abnormal period (the ambient noise period of FIG. 6) and the output matrix to acquire normal output data for the corresponding period.

In other words, the correction module (not illustrated) performs multiplication of a reference matrix which is a transposed matrix for an output matrix defined based on a plurality of outputs to remove the influence (for example, interference, etc. due to the ambient light) due to an unexpected noise reflected in an arbitrary period.

With regard to this, as compared with the sensor of the related art which derives the output value derived from the PPG sensor as single data which does not include spatial information, the PPG sensor 10 disclosed in the present disclosure may provide a plurality of output data so as to estimate spatial information corresponding to a row direction and a column direction and may combine the plurality of output data to a matrix or a vector. Therefore, it is advantageous in that a process of removing a noise in a partial period through a matrix operation or a vector operation for a plurality of output data, by utilizing spatial information reflected to the output data may be easily performed.

Hereinafter, a flow according to a driving method of the present disclosure will be described in brief based on the above-detailed description.

FIG. 8 is a flowchart of an operation of a driving method of a pixelated monolithic photoplethysmographic (PPG) sensor with a spiking neural network structure according to an exemplary embodiment of the present disclosure.

The driving method of a pixelated monolithic photoplethysmographic (PPG) sensor with a spiking neural network structure illustrated in FIG. 8 may be performed by the PPG sensor 10 described above. Accordingly, even though the content is omitted below, the content which has been described for the PPG sensor 10 may also be applied to the description of the driving method of the pixelated monolithic PPG sensor with a spiking neural network structure in the same way.

Referring to FIG. 8, in step S11, the plurality of input neurons 100 may generate a spike signal based on an intensity of received light.

Specifically, in step S11, a light-to-digital converter 110 of each input neuron 100 may generate a spike signal with a strength which is proportional to the intensity of the received light.

Further, the spike signal generated in each input neuron 100 in step S11 may be output to a column input node corresponding to a column direction and a row input node corresponding to a row direction.

Next, in step S12, the plurality of output neurons 200 may add spike signals applied from the plurality of input neurons 100 based on a column direction or a row direction.

Next, in step S13, when the added result through step S12 is equal to or higher than a predetermined reference value, each of the plurality of output neurons 200 may generate an output spike signal.

Next, in step S14, the synchronizer 300 may convert each output spike signal output from each of the plurality of output neurons 200 into a digital signal.

Specifically, in step S14, the synchronizer 300 may convert the output spike signal into a one-bit digital signal synchronized with a clock signal.

In the above description, steps S11 to S14 may be further divided into additional steps or combined as smaller steps depending on an implementation example of the present disclosure. Further, some steps may be omitted if necessary and the order of steps may be changed.

The method for driving a pixelated monolithic photoplethysmographic sensor with a spiking neural network structure according to the exemplary embodiment of the present disclosure may be implemented as a program command which may be executed by various computer means to be recorded in a computer readable medium. The computer readable medium may include solely a program command, a data file, a data structure, and the like or a combination thereof. The program command recorded in the medium may be specifically designed or constructed for the present disclosure or known to those skilled in the art of a computer software to be used. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program command such as a ROM, a RAM, and a flash memory. Examples of the program command include not only a machine language code which is created by a compiler but also a high level language code which may be executed by a computer using an interpreter, etc. The hardware device may be configured to operate as one or more software modules in order to perform the operation of the present disclosure and vice versa.

Further, the above-described method for driving a pixelated monolithic photoplethysmographic sensor with a spiking neural network structure may also be implemented as a computer program or an application executed by a computer which is stored in a recording medium.

The above description of the present disclosure is illustrative only and it is understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

The invention claimed is:

1. A pixelated monolithic photoplethysmographic (PPG) sensor with a spiking neural network structure, comprising:
    a plurality of input neurons which generates a spike signal and is disposed in at least one of a row direction and a column direction;
    a plurality of output neurons which adds the spike signals applied from the plurality of input neurons based on the column direction or the row direction and generates output spike signals when the added result is equal to or higher than a predetermined reference value; and
    a synchronizer which converts each of the output spike signals into a digital signal.

2. The PPG sensor according to claim 1, wherein each of the plurality of input neurons includes:
    a light-to-digital converter which generates the spike signal based on an intensity of received light;
    a first transistor which outputs the spike signal to a column input node corresponding to the column direction; and
    a second transistor which outputs the spike signal to a row input node corresponding to the row direction.

3. The PPG sensor according to claim 2, wherein the light-to-digital converter generates the spike signal with a strength which is proportional to the intensity of the received light.

4. The PPG sensor according to claim 2, wherein the plurality of input neurons is disposed to form an array including n×m pixels, the column input node includes n nodes to which the spike signal generated from m pixels corresponding to each column of the array is applied, and the row input node includes m nodes to which the spike signal generated from n pixels corresponding to each row of the array is applied.

5. The PPG sensor according to claim 4, wherein the plurality of output neurons includes n output neurons each corresponding to any one of columns which form the array and m output neurons each corresponding to any one of rows which form the array.

6. The PPG sensor according to claim 1, wherein the synchronizer converts the output spike signal into a one-bit digital signal which is synchronized with a clock signal.

7. The PPG sensor according to claim 1, wherein relative spatial information of light which is applied to the plurality of input neurons with respect to the PPG sensor is derived based on magnitude information of the digital signal.

8. A driving method of a pixelated monolithic photoplethysmographic (PPG) sensor with a spiking neural network structure, comprising:

generating spike signals based on an intensity of light received by a plurality of input neurons;

adding the spike signals applied from the plurality of input neurons based on a column direction or a row direction;

generating output spike signals by a plurality of output neurons when the added result is equal to or higher than a predetermined reference value; and converting each of the output spike signals into a digital signal.

9. The driving method of a PPG sensor according to claim 8, wherein in the generating of spike signals, a light-to-digital converter generates the spike signal with a strength which is proportional to the intensity of the received light and outputs the spike signal to a column input node corresponding to the column direction and a row input node corresponding to the row direction.

10. The driving method of a PPG sensor according to claim 8, wherein in the converting into a digital signal, the output spike signal is converted into a one-bit digital signal which is synchronized with a clock signal.

* * * * *